(12) United States Patent
Hoogerwerf

(10) Patent No.: US 8,549,894 B2
(45) Date of Patent: Oct. 8, 2013

(54) GAS CHROMATOGRAPHY WITH AMBIENT PRESSURE STABILITY CONTROL

(75) Inventor: Wilhelmus Jacobus Hoogerwerf, Koudekerke (NL)

(73) Assignee: Bruker Chemical Analysis BV, Middleburg (NL)

( * ) Notice: Subject to any disclaimer, the term of this patent is extended or adjusted under 35 U.S.C. 154(b) by 347 days.

(21) Appl. No.: 12/952,984

(22) Filed: Nov. 23, 2010

(65) Prior Publication Data

US 2012/0125083 A1    May 24, 2012

(51) Int. Cl.
*G01N 30/04* (2006.01)
(52) U.S. Cl.
USPC ........................................ 73/23.42
(58) Field of Classification Search
USPC ........................................ 73/23.42
See application file for complete search history.

(56) References Cited

U.S. PATENT DOCUMENTS

| | | | |
|---|---|---|---|
| 4,038,055 A | 7/1977 | Varano et al. | |
| 4,151,741 A | 5/1979 | Schirrmeister | |
| 4,856,319 A * | 8/1989 | Golay | 73/23.35 |
| 5,044,860 A * | 9/1991 | Norem et al. | 414/287 |
| 2002/0178785 A1* | 12/2002 | Lo et al. | 73/23.41 |
| 2003/0108448 A1 | 6/2003 | Sacks et al. | |
| 2005/0160790 A1* | 7/2005 | Tanaka et al. | 73/23.35 |
| 2006/0196247 A1 | 9/2006 | Gamache et al. | |

FOREIGN PATENT DOCUMENTS

EP    0829717 A2    3/1998

* cited by examiner

*Primary Examiner* — Hezron E Williams
*Assistant Examiner* — Nathaniel Kolb
(74) *Attorney, Agent, or Firm* — Robic, LLP

(57) ABSTRACT

In a gas chromatography apparatus, a carrier gas is flowed from a carrier gas supply toward an analytical column at a carrier gas pressure. A sample is added to the carrier gas to form a sample gas. The sample gas is flowed through the analytical column to a gas detector that includes a sample gas outlet communicating with a gas buffer vessel. The carrier gas pressure is controlled relative to a buffer pressure of the gas buffer vessel.

14 Claims, 2 Drawing Sheets

GAS CHROMATOGRAPHY WITH AMBIENT PRESSURE STABILITY CONTROL

BACKGROUND

The present invention relates generally to gas chromatography and particularly to controlling the operating pressure of the pneumatic portion of a gas chromatography apparatus. Gas chromatography (GC) entails the analytical separation of a vaporized or gas-phase sample. In a GC system, a chemically inert carrier gas such as hydrogen, helium or nitrogen is utilized as the mobile phase for elution of the analyte sample in an analytical (or sample) column. The carrier gas is introduced into the system upstream of the analytical column. The sample is typically injected into the gas stream at or near the head of the analytical column and is thus carried by the carrier gas through the analytical column. The analytical column is typically housed in a thermally controlled oven or alternatively may be directly heated such as by controlled electrically resistive heating means. The analytical column may be constructed of stainless steel, glass, fused silica, Teflon®, or the like. The analytical column may be of the packed or open tubular (capillary) type. The analytical column contains a stationary phase (particles, films or layers of a selected composition) by which different components of the sample are retained differently. Thus, as the sample flows through the analytical column it becomes separated into discrete components of differing analytical (qualitative and/or quantitative) significance. The eluent from the analytical column flows to a gas detector provided with the GC system. Various types of detectors may be employed such as, for example, a flame ionization detector (FIO), thermal conductivity detector (TCD), etc. The choice of detector often depends on the sample being analyzed. Moreover, the type of carrier gas utilized often depends on the type of detector utilized. Additionally, depending on detector design, the carrier gas may be utilized as a reference gas by also flowing the carrier gas through a separate reference column (not containing the sample) to the gas detector under the same conditions (e.g., temperature, pressure, stationary phase, etc.) as the analytical column. Generally, the gas detector is of a type responsive to a property of the separated analytes (e.g., concentration) and converts the outputted flow of separated analytes to electrical measurement signals, which are then transmitted to a data processor. The data processor derives peak information or other useful analytical information from the measurement signals received. When a reference column is utilized, measurements of the eluent of the reference column are also taken into account in the data acquisition.

A GC system typically utilizes one or more gas flow (flow rate and/or pressure) controllers to control (switch on and off) the flow of carrier gas to the GC column. For the GC system to operate properly, the carrier gas must flow through a GC column at a particular working pressure (i.e., column head pressure). The gas flow controller(s) may be of either the mechanical or electronic type. Conventionally, both types of gas flow controllers regulate pressure relative to ambient pressure, thus making them susceptible to short-term ambient pressure fluctuations caused by natural conditions (wind, drafts) or other conditions (e.g., opening/closing doors in a laboratory, etc.). From the perspective of data acquisition, these pressure fluctuations cause disturbed baselines and high noise levels, which in turn result in higher detection limits and reduced repeatability of results. These problems have been particularly noted in cases where a GC system utilizes a TCD as the detector. A TCD typically includes ambient pressure outlets, thereby making the detector also susceptible to ambient pressure fluctuations. In addition, capillary GC systems in which the carrier gas flows are very low are particularly sensitive to ambient pressure fluctuations.

FIG. 1 is a schematic view of an example of a conventional GC system 100. A carrier gas supply 104 is operated to establish a flow of carrier gas to a gas flow controller 108 (typically a pressure controller). In this example, the original carrier gas flow is split into two carrier gas flows, either by the gas flow controller 108 or by a separate flow splitter (not shown). One of the carrier gas flows is inputted to an analytical column 112 while the other carrier gas flow is inputted to a reference column 116. The columns 112, 116 are enclosed in a suitable housing (not shown), which may include an oven as noted above. A sample injector 120 positioned at or near the head of the analytical column 112 introduces a gas-phase or vaporized sample into the carrier gas flow, whereby a sample-bearing (sample and carrier) gas is flowed through the analytical column 112 while a carrier-only gas is flowed through the reference column 116. The respective distal ends of the analytical column 112 and the reference column 116 are fluidly connected to a TCD 124. The TCD 124 receives the analytically separated sample gas effluent and the reference gas effluent, generates electrical signals based on measurements of thermal conductivity, and transmits the signals to a data acquisition system 128 for further processing, readout/display, etc. By way of background, the TCD 124 typically includes a four-element Wheatstone bridge in which the sensing elements are temperature-sensitive (e.g., resistive filaments, semiconducting thermistors, etc.). Some of the sensing elements are exposed to the sample gas flow while the other sensing elements are exposed to the reference gas flow. The resistances of the sensing elements vary in response to temperature changes. The temperature of each sensing element depends on the thermal conductivity of the sample gas or reference gas flowing around the sensing element. Thermal conductivity in turn depends on gas composition and thus may be correlated to the concentration of a particular gas molecule. The TCD 124 in this case is arranged such that the thermal conductivity of the reference gas (i.e., the carrier gas component of the sample gas as well as the carrier gas-only reference gas) is canceled out from the measurement signal outputted to the data acquisition system 128. Among other tasks, the data acquisition system 128 correlates the measurement signals to the concentration of the sample gas as it flows in analytically separated form from the analytical column 112, thereby enabling the generation of information-rich sample peaks the data output.

Of particular note for purposes of the present subject matter, the pressure controller 108 includes an ambient pressure reference channel 132 and the TCD 124 includes a sample gas outlet vent 134 and a reference gas outlet vent 136. These features allow gases to vent to atmosphere, whereby the entire pneumatic system of the GC system 100 essentially operates as an open system that is exposed to the ambient conditions in which the GC system 100 resides. It thus can be seen that the conventional GC system 100 is highly susceptible to ambient conditions, particularly the pressure fluctuations that may occur as described above. Prior solutions to minimizing the influence of ambient pressure fluctuations have been mainly focused on reducing ambient pressure fluctuations in the direct environment in which the GC system 100 operates (e.g., reducing air currents in the laboratory) and not on making improvements to the GC system 100 itself.

In view of the foregoing, there is a need for providing GC apparatus and methods that render the deleterious effects of ambient pressure fluctuations negligible.

SUMMARY

To address the foregoing problems, in whole or in part, and/or other problems that may have been observed by persons skilled in the art, the present disclosure provides apparatus, devices, systems, instruments, or methods or processes, as described by way of example in implementations set forth below.

According to one implementation, a gas chromatography apparatus includes an analytical column, a sample gas introduction device communicating with the analytical column, and a gas pressure controller including a carrier gas inlet, a carrier gas outlet communicating with the sample gas introduction device, and a gas pressure reference outlet. The apparatus further includes a gas detector including a sample gas inlet communicating with the analytical column and a sample gas outlet, and a gas buffer vessel communicating with the gas pressure reference outlet and the sample gas outlet. The gas buffer vessel includes a gas buffer outlet. The apparatus further includes a gas outlet valve configured for switching the gas buffer outlet between an open condition in which the pressure controller, the detector and the gas buffer vessel are in fluid communication with an ambient environment surrounding the gas chromatography apparatus, and a closed condition in which the pressure controller, the detector and the gas buffer vessel are fluidly isolated from the ambient environment.

According to another implementation, the apparatus further includes a system controller communicating with the gas outlet valve and configured for actuating the gas outlet valve between the open and closed conditions in coordination with controlling the sample introduction device.

According to another implementation, a method is provided for operating a gas chromatography apparatus. A carrier gas is flowed from a carrier gas supply toward an analytical column at a carrier gas pressure. A sample is added to the carrier gas to form a sample gas. The sample gas is flowed through the analytical column to a gas detector that includes a sample gas outlet communicating with a gas buffer vessel. The carrier gas pressure is controlled relative to a buffer pressure of the gas buffer vessel.

According to another implementation, controlling the carrier gas pressure includes operating a gas pressure controller interposed between the carrier gas supply and the analytical column and fluidly communicating with the gas buffer vessel.

According to another implementation, controlling the carrier gas pressure includes fluidly isolating the pressure controller, the gas detector and the gas buffer vessel from an ambient environment external to the gas chromatography apparatus.

According to another implementation, controlling the carrier gas pressure includes switching a gas outlet valve of the gas buffer vessel from an open position to a closed position, wherein at the open position the detector and the gas buffer vessel are in fluid communication with an ambient environment external to the gas chromatography apparatus, and at the closed position the detector and the gas buffer vessel are fluidly isolated from the ambient environment.

According to another implementation, the carrier gas may also be flowed from the carrier gas supply through a reference column and to the gas detector. Controlling the carrier gas pressure may include operating a gas pressure controller to control respective carrier gas flows from the carrier gas supply to the analytical column and to the reference column, venting carrier gas from the gas pressure controller to the gas buffer vessel, venting sample gas from the sample gas outlet to the gas buffer vessel, and venting reference gas from a reference gas outlet of the gas detector to the gas buffer vessel.

According to another aspect of any of the apparatus or methods disclosed herein, chromatographic data is acquired from a sample based on measurements of the sample gas taken at the gas detector.

Other apparatus, devices, systems, methods, features and/or advantages of the invention will be or will become apparent to one with skill in the art upon examination of the following figures and detailed description. It is intended that all such additional apparatus, devices, systems, methods, features and/or advantages be included within this description, be within the scope of the invention, and be protected by the accompanying claims.

DETAILED DESCRIPTION

Figure 1:
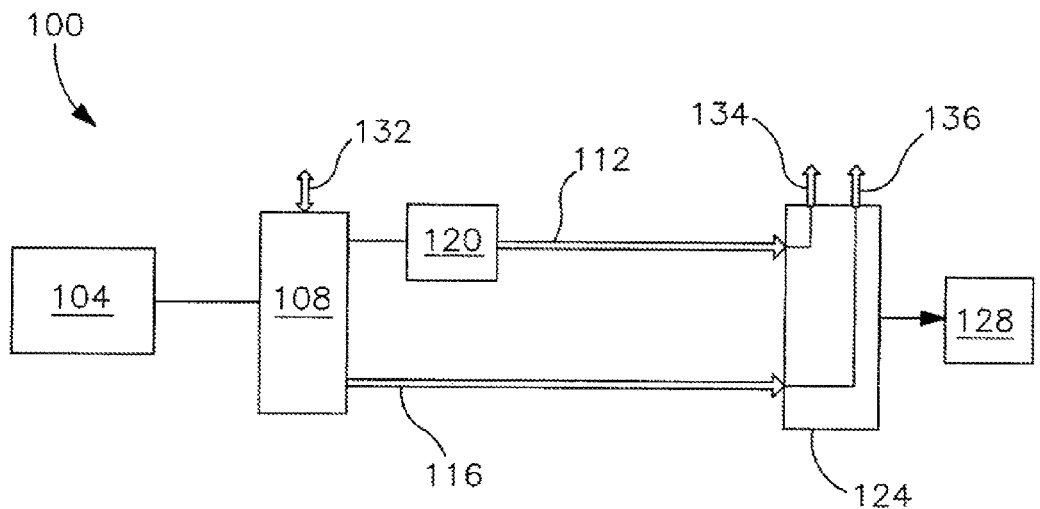
FIG. 1 is a schematic view of an example of a gas chromatographic system according to a conventional design.
Figure 2:
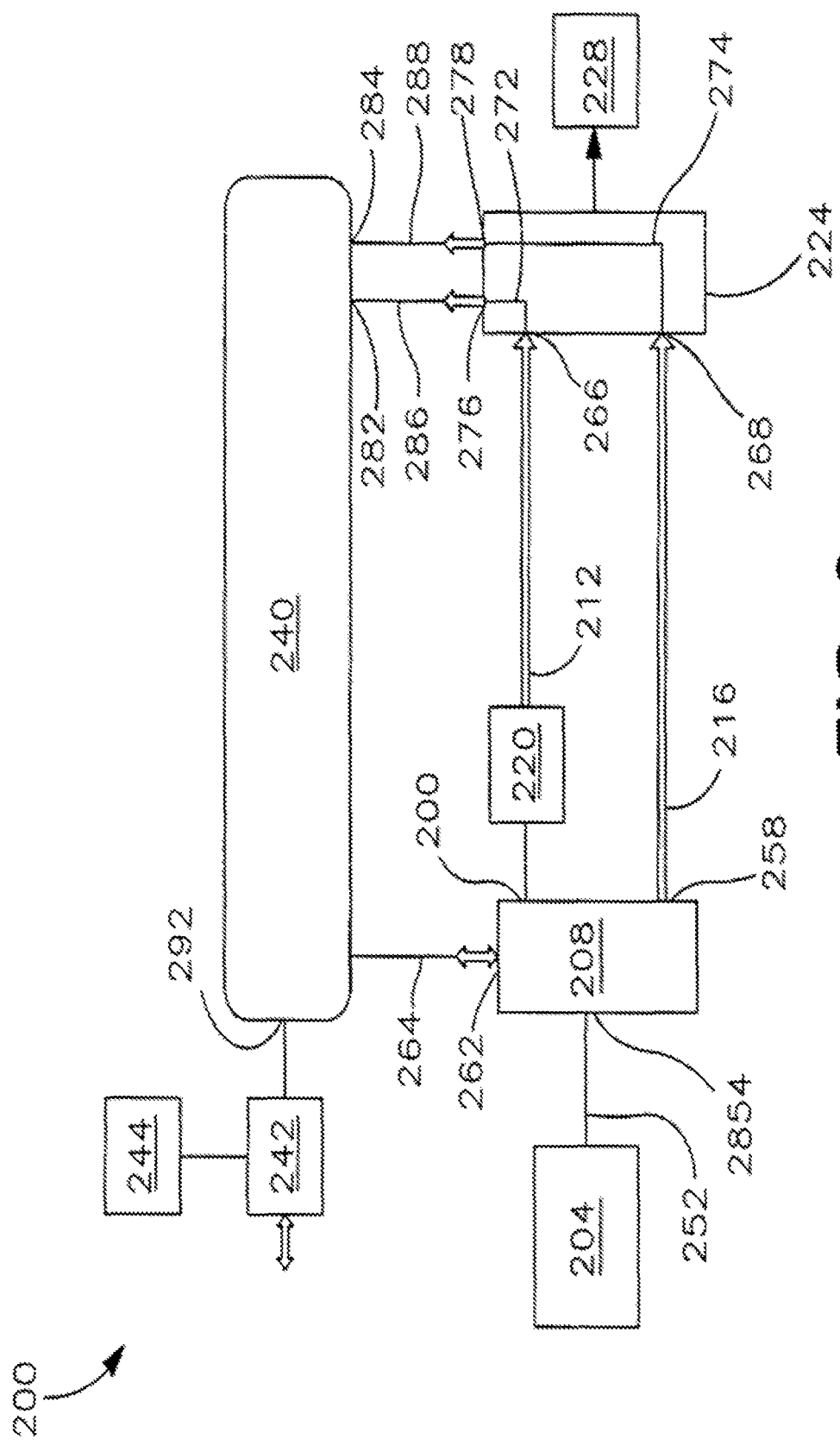
FIG. 2 is a schematic view of an example of a gas chromatographic system according to an implementation of the present invention.

FIG. 2 is a schematic view of an example of a gas chromatograph (GC) apparatus or system 200 according to an implementation of the present invention. it will be understood that FIG. 2 is a highly simplified schematic illustration that includes a few basic components of the GC apparatus 200. For simplicity, additional components, features and details that may be necessary for practical implementation of the GC apparatus 200 are not specifically shown but readily appreciated by persons skilled in the art. Also for simplicity, components similar to those illustrated in FIG. 1 are designated with similar reference numerals with the understanding that such components may be modified or adapted as necessary for carrying out the present teaching.

In the present example, the GC apparatus 200 generally includes a carrier gas supply 204, one or more gas flow controllers 208, an analytical or sample column 212, a reference column 216, a sample introduction device 220, a gas detector 224, a data acquisition system 228, a gas buffer vessel 240, a gas buffer outlet valve 242, and a system controller 244. The carrier gas supply 204 may be any suitable device or system for establishing a flow of a suitable carrier gas (e.g., hydrogen, helium, nitrogen, etc.) through a carrier gas supply line 252 (e.g., a suitable conduit such as a tube or pipe) to the GC columns 212,216, as regulated by the gas flow controller 208. As noted above, the GC columns 212, 216 may be enclosed in an enclosure (not shown) that often functions as an oven for heating the GC columns 212, 216 or alternatively may be heated by direct means. A portion of one or both GC columns 212, 216 may be coiled to accommodate a desired length while minimizing the size of the enclosure. The gas flow controller 208 includes a carrier gas input 254 for receiving the supply of carrier gas and a carrier gas output for flowing carrier gas to the analytical column 212. In the present example in which a reference gas is utilized, the carrier gas output includes a first carrier gas output 256 for flowing carrier gas to the analytical column 212 and a second carrier gas output 258 for flowing carrier gas to the reference column 216. The present example assumes that the gas flow controller 208 implements the splitting of the carrier gas into the two separate streams. It will be understood, however, that a distinct flow splitter may be placed in fluid communication with the gas flow controller 208 in which case the first carrier gas output 256 and the second carrier gas output 258 may be considered as being the outputs of the flow splitter. In the schematic illustration, the gas flow controller 208 may represent one or more components (e.g., pressure regulator, flow controller, etc.). Generally, the gas flow controller 208 may have any suitable design that is capable of switching the flow of carrier gas between on and off states and regulating flow rate, typically by regulating pressure. The gas flow controller 208 may also be capable of sensing the carrier gas pressure and providing a readout signal thereof. In accordance with the present teachings, the gas flow controller 208 further includes a gas pressure reference outlet 262, which fluidly communicates with the gas buffer vessel 240 either directly or via a gas line 264.

The sample introduction device 220 may include a syringe or other fluid moving means to inject an analyte sample into the first carrier gas flow from the gas flow controller 208, whereby a flow of sample gas (containing both sample and carrier gas components) enters the analytical column 212. Sample injection may be carried out on an automated, semi-automated, or manual basis. In the present example in which a reference gas is measured, the gas detector 224 includes both a sample gas inlet 266 fluidly communicating with the outlet of the analytical column 212 and a reference gas inlet 268 fluidly communicating with the outlet of the reference column 216. The eluted components from the GC columns 212, 216 flow through respective internal passages 272, 274 of the detector where the temperature-sensitive elements are located and exit the detector 224 via a respective sample gas outlet 276 and a reference gas outlet 278. In accordance with the present teachings, the sample gas outlet 276 and the reference gas outlet 278 fluidly communicate with respective inlets 282, 284 of the gas buffer vessel 240 either directly or via respective gas lines 286, 288. The gas detector 224 in the present example may be a TCD.

The gas buffer vessel 240 may be any gas-tight container of sufficient internal volume to receive gas flows from the gas pressure reference outlet 262 of the pressure controller 208 and from the sample gas outlet 276 and the reference gas outlet 278 of the gas detector 208, while maintaining a gas pressure suitable for the chromatographic operations implemented by the GC apparatus 200. The gas buffer vessel 240 includes a gas buffer outlet 292. The gas outlet valve 242 controls fluid flow through the gas buffer outlet 292. For this purpose, the gas outlet valve 242 may be any type of valve capable of being actuated between open and closed positions (or conditions, states, etc.). In one non-limiting example, the gas outlet valve 242 may be a solenoid valve. In the open position, the interior of the gas buffer vessel 240 is exposed to the ambient environment via the gas buffer outlet 292. Hence, the pressure controller 208, the gas detector 224 and associated gas lines 264, 286, 288 are likewise exposed to the ambient environment. In the closed position, the gas buffer outlet 292 is closed off from the ambient environment and consequently the internal pneumatics of the GC system 200 (i.e., the gas buffer vessel 240, pressure controller 208, gas detector 224, gas lines 264, 286, 288, etc.) is fluidly isolated from the ambient environment.

As an example of implementing a method for operating the GC system 200, the gas outlet valve 242 may be switched to the closed position during a run mode of operation (i.e., during the running of a chromatography experiment) and switched to the open position during a non-run mode of operation (i.e., a period during which the acquisition of chromatographic data is not desired). Prior to the initiation of a chromatography run, the GC system 200 may initially be in the non-run mode. With the gas buffer outlet 292 open, the pressure inside the gas buffer vessel 240 equals the ambient pressure and thus the gas pressure reference outlet 262, the sample gas outlet 276 and the reference gas outlet 278 are likewise at ambient pressure. Subsequently, at the start of a chromatography run the GC system 200 is switched to the run mode by actuating the gas outlet valve 242 to close the gas buffer outlet 292, after which point the GC system 200 operates as a closed system relative to the pressure inside the gas buffer vessel 240, and the gas pressure reference outlet 262, the sample gas outlet 276 and the reference gas outlet 278 are no longer influenced by ambient pressure fluctuations. The carrier gas supply 204, sample introduction device 220, gas detector 224 and data acquisition system 228 may then be operated in the usual manner for implementing the desired chromatographic analysis of a sample material. It will be noted that the carrier gas flowing into the GC system 200 from the external gas supply 204 will be vented into the gas buffer vessel 240, causing a slight increase in pressure inside the vessel 240 over the course of the analysis time. By choosing the proper dimensions of the gas buffer vessel 240 in relation to the carrier gas flow rate and the analysis time, this pressure increase will be minimal and will not result in an erratically disturbed baseline. Moreover, as a result of the configuration taught herein, the pressure controller 208 now controls the carrier gas pressure relative to the pressure inside the gas buffer vessel 240 (not relative to ambient), thereby keeping the pressure drop across the analytical system constant.

The GC apparatus 200 may also include a suitable system controller 244 that is configured to switch the GC apparatus 200 between the run and non-run modes of operation and control one or more of the operative components above during each mode of operation. The system controller 244 may be electronic processor-based and may be capable of executing instructions contained in software. Thus, for instance, the system controller 244 may be an electronic controller such as a microcontroller, microprocessor, application specific integrated circuit (ASIC), digital signal processor (DSP), computer (e.g., personal computer, networked client terminal, handheld computing device, etc.), or the like, and may be capable of receiving and/or sending various types of electrical signals such as data signals, measurement signals, and timing and control signals. Generally, the system controller 244 schematically illustrated in FIG. 2 may include hardware, firmware, software, or a combination of two or more of the foregoing. The system controller 244 may communicate with various components of the GC system 200 via wired or wireless communication links. In particular, the system controller 244 is configured for transmitting control signals to the gas outlet valve 242 to actuate the gas outlet valve 242 between the open and closed positions. The system controller 244 may also communicate (not shown) with other components such as the carrier gas supply 204, sample introduction device 220, pressure controller 208, gas detector 224, and data acquisition system 228 as needed for coordinating or synchronizing their respective operations with that of the gas outlet valve 242. One or more operations of the system controller 244 may be controlled by direct user input or by programmed instructions.

While the example relating to FIG. 2 utilizes a TCD as a detector, it will be understood that the subject matter disclosed herein is not limited to any particular type of detector. The subject matter taught herein has been found particularly useful in GC systems utilizing a TCD. However, GC systems utilizing other types of detectors that conventionally rely on venting gases to atmosphere may also benefit from implementation of the present subject matter.

Figure 3:
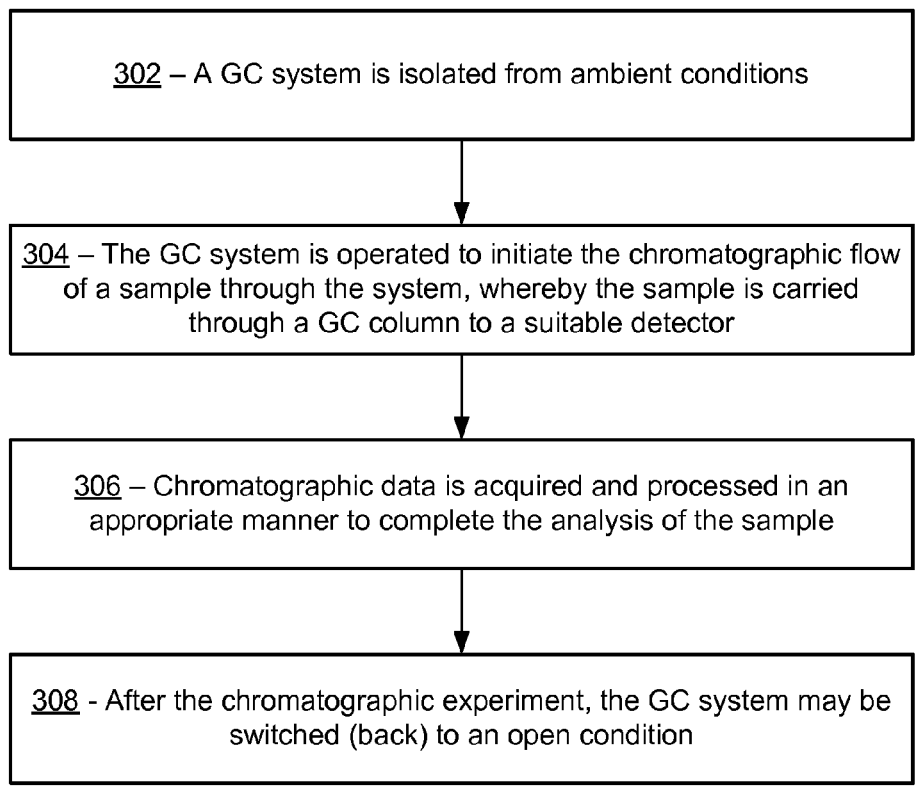
FIG. 3 is a flow diagram illustrating an example of a method provided in accordance with the present invention.

FIG. 3 is a flow diagram 300 illustrating an example of a method provided in accordance with the present invention. The flow diagram 300 may also represent an apparatus or system configured for performing the illustrated method. At block 302, a GC system is isolated from ambient conditions. This may entail switching the GC system from an open condition in which the GC system is exposed to ambient pressure conditions to a closed condition in which the effects of ambient pressure conditions are eliminated or at least significantly reduced or rendered negligible. At block 304, the GC system is then operated to initiate the chromatographic flow of a sample through the system, whereby the sample is carried through a GC column to a suitable detector. At block 306, chromatographic data is acquired and processed in an appropriate manner to complete the analysis of the sample. The activities associated with blocks 304 and 306 occur while the GC system is maintained in the ambient-isolated state and thus are shielded from the adverse effects of ambient pressure perturbations. During this time, the flow of carrier gas through the system may be controlled relative to the internal gas pressure of the system, i.e., without needing to rely on ambient pressure as a reference. Also during this time, gases may be prevented from being vented to atmosphere. At block 308, after the chromatographic experiment the GC system may be switched (back) to an open condition. As noted above, FIG. 3 may represent an example of an apparatus or system 300 capable of performing the illustrated method. Accordingly, the blocks 302-308 may be considered as depicting one or more means for performing the functions or steps corresponding to those blocks 302-308 and just described. An example of such an apparatus is described above and illustrated in FIG. 2.

In general, the term "communicate" (for example, a first component "communicates with" or "is in communication with" a second component) is used herein to indicate a structural, functional, mechanical, electrical, optical, magnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A gas chromatography apparatus, comprising:
an analytical column;
a sample gas introduction device communicating with the analytical column;
a gas pressure controller comprising a carrier gas inlet, a carrier gas outlet communicating with the sample gas introduction device and a gas pressure reference outlet;
a gas detector comprising a sample gas inlet communicating with the analytical column and a sample gas outlet;
a gas buffer vessel communicating with the gas pressure reference outlet and the sample gas outlet, the gas buffer vessel comprising a gas buffer outlet; and
a gas outlet valve configured for switching the gas buffer outlet between an open condition in a period during which an acquisition of chromatographic data is not desired, in which open condition the pressure controller, the detector and the gas buffer vessel are in fluid communication with an ambient environment surrounding the gas chromatography apparatus, and a closed condition during a run of a chromatography experiment, in which closed condition the pressure controller, the detector and the gas buffer vessel are fluidly isolated from the ambient environment.

2. The gas chromatography apparatus of claim 1, further comprising a reference column, wherein the carrier gas outlet of the gas pressure controller comprises a first carrier gas outlet communicating with the analytical column and a second carrier gas outlet communicating with the reference column, and the gas detector further comprises a reference gas inlet communicating with the reference column and a reference gas outlet communicating with the gas buffer vessel.

3. The gas chromatography apparatus of claim 1, wherein the gas detector is a thermal conductivity detector.

4. The gas chromatography apparatus of claim 1, further comprising a system controller communicating with the gas outlet valve and configured for actuating the gas outlet valve between the open and closed conditions in coordination with controlling the sample introduction device.

5. A method for operating a gas chromatography apparatus, the method comprising:
flowing a carrier gas from a carrier gas supply toward an analytical column at a carrier gas pressure;
adding a sample to the carrier gas to form a sample gas;
flowing the sample gas through the analytical column to a gas detector, the gas detector comprising a sample gas outlet communicating with a gas buffer vessel; and
controlling the carrier gas pressure relative to a buffer pressure of the gas buffer vessel, wherein controlling the carrier gas pressure comprises switching a gas outlet valve of the gas buffer vessel from an open position in a period during which an acquisition of chromatographic data is not desired to a closed position during a run of a chromatography experiment, wherein at the open position the detector and the gas buffer vessel are in fluid communication with an ambient environment external to the gas chromatography apparatus, and at the closed position the detector and the gas buffer vessel are fluidly isolated from the ambient environment.

6. The method of claim 5, wherein controlling the carrier gas pressure comprises operating a gas pressure controller interposed between the carrier gas supply and the analytical column and communicating with the gas buffer vessel as to use the buffer pressure as reference pressure.

7. The method of claim 5, wherein controlling the carrier gas pressure comprises operating a gas pressure controller interposed between the carrier gas supply and the analytical column and communicating with the gas buffer vessel as to use the buffer pressure as reference pressure, and venting sample gas from the sample gas outlet to the gas buffer vessel.

8. The method of claim 5, wherein controlling the carrier gas pressure comprises operating a gas pressure controller interposed between the carrier gas supply and the analytical column and communicating with the gas buffer vessel as to use the buffer pressure as reference pressure, and fluidly isolating the pressure controller, the gas detector and the gas buffer vessel from an ambient environment external to the gas chromatography apparatus.

9. The method of claim 5, further comprising permitting the buffer pressure to increase above an ambient pressure of the ambient environment while the gas outlet valve is in the closed position.

10. The method of claim 5, further comprising ceasing the flow of sample gas through the analytical column, and switching the gas outlet valve from the closed position to the open position.

11. The method of claim 5, further comprising switching the gas outlet valve in timed coordination with flowing the carrier gas and adding the sample.

12. The method of claim 5, further comprising flowing the carrier gas from the carrier gas supply through a reference column and to the gas detector.

13. The method of claim 5, further comprising flowing the carrier gas from the carrier gas supply through a reference column and to the gas detector, wherein controlling the carrier gas pressure comprises operating a gas pressure controller to control respective carrier gas flows from the carrier gas supply to the analytical column and to the reference column, venting sample gas from the sample gas outlet to the gas buffer vessel, and venting reference gas from a reference gas outlet of the gas detector to the gas buffer vessel.

14. The method of claim 5, further comprising operating the gas detector by measuring a thermal conductivity of the sample gas.

\* \* \* \* \*